(12) United States Patent
Boyle et al.

(10) Patent No.: US 7,355,415 B2
(45) Date of Patent: Apr. 8, 2008

(54) METHOD FOR ON-LINE MONITORING OF CONDITION OF NON-AQUEOUS FLUIDS

(75) Inventors: Frederick P. Boyle, Kirtland, OH (US); Vadim F. Lvovich, Cleveland Heights, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 11/530,063

(22) Filed: Sep. 8, 2006

(65) Prior Publication Data

US 2007/0151806 A1 Jul. 5, 2007

Related U.S. Application Data

(63) Continuation-in-part of application No. 10/841,757, filed on May 7, 2004, now abandoned.

(51) Int. Cl.
*G01R 27/08* (2006.01)

(52) U.S. Cl. ....................... 324/707; 324/698

(58) Field of Classification Search ............... 324/698, 324/707
See application file for complete search history.

(56) References Cited

U.S. PATENT DOCUMENTS

| 4,733,556 A | 3/1988 | Meitzler et al. ............ 73/64 |
| 5,331,287 A | 7/1994 | Yamagishi et al. ......... 324/724 |
| 5,518,590 A | 5/1996 | Fang .................... 205/780.5 |
| 5,540,086 A | 7/1996 | Park et al. ................ 73/53.05 |
| 5,656,767 A | 8/1997 | Garvey, III et al. ........ 73/61.44 |
| 5,824,889 A | 10/1998 | Park et al. .................... 73/116 |
| 5,889,200 A | 3/1999 | Centers et al. ............. 73/53.01 |
| 5,933,016 A | 8/1999 | Kauffman et al. .......... 324/698 |
| 6,028,433 A | 2/2000 | Cheiky-Zelina et al. .... 324/663 |
| 6,217,745 B1 | 4/2001 | Fang ......................... 205/775 |
| 6,268,737 B1 | 7/2001 | Marszalek .................. 324/663 |
| 6,535,001 B1 | 3/2003 | Wang ......................... 324/698 |
| 2004/0036487 A1 | 2/2004 | Heremans et al. .......... 324/698 |

(Continued)

FOREIGN PATENT DOCUMENTS

EP 0531585 A1 3/1993

(Continued)

OTHER PUBLICATIONS

Electrical Conductivity Method for Evaluation of Oxidative Degradation of Oil Lubricants; Lubrication Engineering, vol. 48, 7, 539-544; 1991, by Atsushi Sato and Takashi Oshika.

(Continued)

*Primary Examiner*—Andrew H. Hirshfeld
*Assistant Examiner*—Timothy J Dole
(74) *Attorney, Agent, or Firm*—Teresan W. Gilbert; Christopher D. Hilker

(57) ABSTRACT

A method for determining a condition of a highly resistive fluid in transportation and industrial equipment. The method is suitable for determining the condition of a non-aqueous fluid including applying a high-frequency voltage signal between electrodes immersed in the fluid, measuring the fluid's response to the applied signal and determining a fluid property, and comparing the magnitude of the determined property, relative to the magnitude of that property when the fluid is fresh.

14 Claims, 6 Drawing Sheets

U.S. PATENT DOCUMENTS

2004/0075448 A1    4/2004    Lvovich et al. ............. 324/707

FOREIGN PATENT DOCUMENTS

| | | |
|---|---|---|
| EP | 1014082 A2 | 6/2000 |
| JP | 406082408 | 3/1994 |
| WO | WO 91/09922 | 7/1991 |

OTHER PUBLICATIONS

Development of an On-Board Type Oil Deterioration Sensor; SAE Technical Paper Series, Oct. 1993.

Proceedings of the Symposium on Chemical Sensors; The Electrochemical Society, Inc., Proceedings vol. 87-9; Turner, no date.

In-Situ Oil Condition Monitoring in Passenger Cars; Lubrication Engineering, vol. 50, 8, 605-611; Lee et al., 1993.

Development of an Automatic Engine Oil-Change Indicator System; SAE Technical Paper Series; Schwartz et al.; Feb. 23-27, 1987.

A Capacitive Oil Deterioration Sensor; Saloka et al., no date.

Oil Maintenance Tester: A New Device to Detect the Degradation Level of Oils; Lubrication Engineering; Nov. 1986; Kato et al.

In Situ Electrochemical Sensor for Measurement in Nonconductive Liquids; J. Electrochemical Society, vol. 140, No. 3, Mar. 1993; Joseph et al.

The development of in situ electrochemical oil-condition sensors; Sensors and Actuators B, 17 (1994) 179-185; Wang et al.

In situ monitoring of high-temperature degraded engine oil condition with microsensors; Sensors and Actuators B, 20 (1994) 49-54; Lee et al.

The application of a.c. impedance technique for detecting glycol contamination in engine oil; Sensors and Actuators B 40 (1997) 193-197; Want et al.

"Smart Sensing" of Oil Degradation and Oil Level Measurements in Gasoline Engines; SAE Technical Paper Series; Mar. 6-9, 2000; Basu et al.

Development of an On-Board Type Oil Deterioration Sensor; SAE Technical Paper Series; Oct. 18-21, 1993; Morishita et al.

Low Cost Oil Deterioration Sensor for On-Board Diagnostics; Park et al., no date.

"Electrical Techniques for Monitoring the Condition of Lubrication Oil", Turner, J.D. et al., (Measurement Science and Technology, IOP Publishing, Bristol, GB, vol. 14, No. 10, Oct. 2003, pp. 1794-1800, XP-001208864).

Corresponding PCT Search Report for International Application No. PCT/US2005/015185; date of mailing of search report: Jul. 8, 2005.

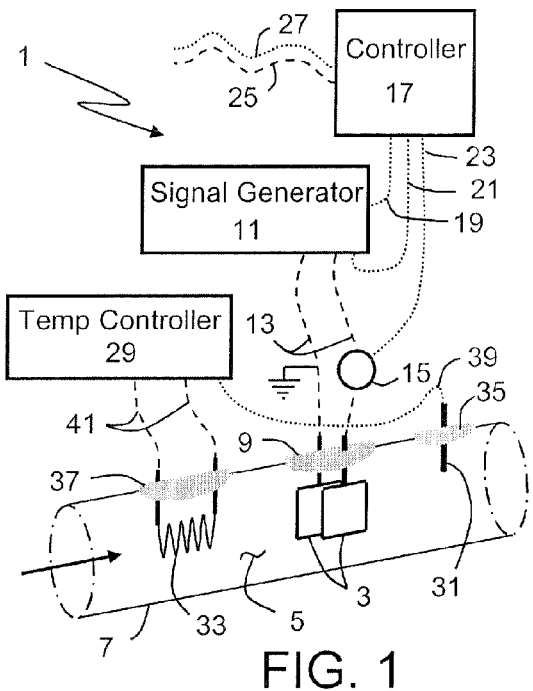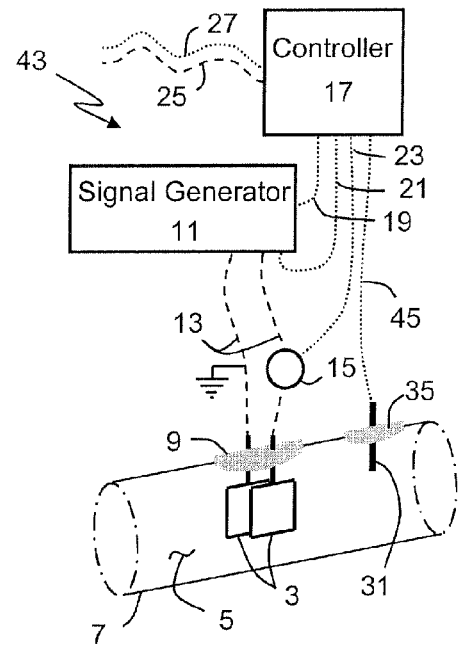
FIG. 1
FIG. 2
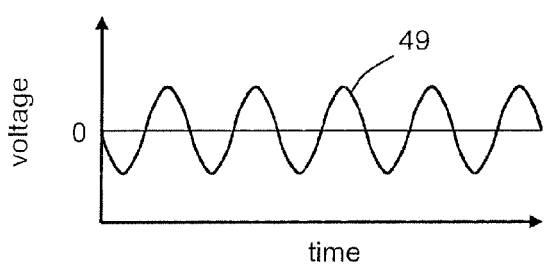
FIG. 3
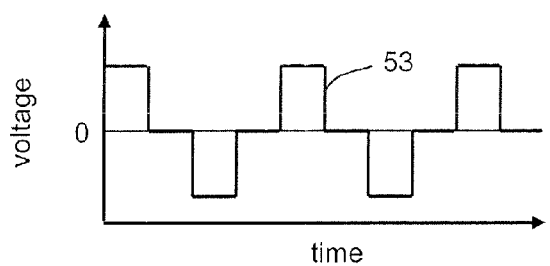
FIG. 4

METHOD FOR ON-LINE MONITORING OF CONDITION OF NON-AQUEOUS FLUIDS

This application is a continuation-in-part of U.S. Ser. No. 10/841,757 filed May 7, 2004 now abandoned and claims the benefit of said prior application.

BACKGROUND OF THE INVENTION

The present invention is a method for monitoring the condition of a highly resistive fluid(s) while in use in transportation or industrial equipment including but not limited to vehicles, machines, devices and the like. The invention has particular benefit for on-line monitoring and analysis of a diesel engine lubricant condition. More specifically, the invention has benefit in monitoring soot content of a diesel engine lubricant and in determining when the lubricant loses the ability to control the soot content for optimum engine performance and life.

Lubricating oil is critical to the life and performance of an internal combustion engine. When the lubricant has appropriate viscosity for the required hydrodynamic film, detergents and dispersants to suspend and/or neutralize undesired contaminants, and surface active chemicals to protect engine component surfaces, the lubricant allows for long, efficient engine operation by reducing friction, wear and corrosion of engine components. In general, a lubricant's performance characteristics change with use and age as the base oil and/or additives are consumed, degraded or depleted. A lubricant reaches the end of its useful life when any one of the lubricant's performance properties is outside a desired range. Using a lubricant past the end of its useful life reduces engine life and performance and possibly leads to catastrophic engine failure.

Lubricant value is maximized if used lubricant remains in an engine and is not replaced with fresh, i.e. unused, lubricant until the lubricant reaches the end of its useful life. However, due to the complexity of lubricant degradation, which can be a function of engine age, operating conditions and other factors, accurate determination of lubricant condition has traditionally required off-line laboratory tests which often are not cost and/or time effective for equipment operators. Hence, most operators simply estimate lubricant condition and change lubricant based on one or more easily measured engine operating parameters such as time of operation, mileage driven, fuel use or others, or they rely on algorithms by engine manufacturers that typically use one or more engine operating parameters, but no actual lubricant measurement. An issue with estimates or algorithms that use no lubricant condition measurement or specific information about the quality of the lubricant in the engine is that lubricant change decisions are made without knowing either actual condition or even potential useful life. Actual lubricant condition or potential life information is particularly important in lubricant change decisions for engines where contaminants such as soot play a major role in lubricant degradation since individual lubricants can vary widely in their ability to suspend and/or neutralize contaminants.

Recently sensors for real-time, on-board measurement of a lubricant's electrical, optical or other properties have been introduced; a good overview is given in "Determining Proper Oil and Filter Change Intervals: Can Onboard Automotive Sensors Help?", Sabrin Khaled Gebarin and Jim Fitch, Practicing Oil Analysis, March-April 2004. Many of these sensors simply provide an output that is function of the measured lubricant property with no actual analysis of fluid condition. In general, sensors that do not provide a "fluid condition" output are of limited value to engine/equipment manufacturers who do not know the relationship, if any, between sensor signal and fluid condition. To overcome this limitation, some sensors attempt to provide a complete solution with hardware and/or software that interpret a fluid condition based on measured lubricant property. U.S. application Ser. No. 10/271,885, filed Oct. 16, 2002 entitled "Method for on-line monitoring of quality and condition of non-aqueous fluids", Lvovich, et al. is a method for a relatively complete fluid condition analysis based a multitude of a fluid's electrical impedance responses. While the relatively complete fluid condition analysis is appropriate in some fluid applications, other applications require a more cost effective solution for interpretation of only a particular fluid condition; for example, diesel engine manufacturers and end-users have interest in monitoring soot related properties in the engine's lubricant. A lubricant's soot content, which is a consequence of the diesel engines' combustion process, provides information about the engine's operating condition, but more importantly, knowing if the lubricant is of appropriate condition to effectively maintain the soot in a stable suspension of finely dispersed particles is important to optimize oil change intervals.

US application 2004/0036487, entitled "Diesel engine lubricating oil contaminant sensor method", to Heremans, et al. describes a sensor that attempts to meet the need for monitoring the soot content of the lubricant in a diesel engine. A limitation is that while the described sensor may measure lubricant soot content, the sensor does not determine if or when the lubricant begins to lose effectiveness in controlling the soot; that is, the point at which the additional soot content results in increased size of dispersed particles. A loss of a lubricant's ability to control soot, or more generally contaminants, is typically first identified by increased fluid viscosity, but typically occurs before a rapid viscosity increase is noted and, in any case leads, to reduced performance and service life of the engine.

Hence, there remains a need for an on-line fluid monitoring sensor to "real-time" determine not only of fluid contaminant, in particular soot, content but of when the fluid begins to lose its ability to suspend, disperse or otherwise control the contaminant in order that the fluid can be maintained to provide desired equipment performance and life.

Accordingly, the present invention provides a sensor with a method for on-line determining fluid condition based on a property that is consistent with contaminant content and when the fluid loses the capability of controlling contaminants while the fluid is in use in industrial or transportation applications.

SUMMARY OF THE INVENTION

The present invention relates to a method to monitor contaminants in lubricants used in transportation and industrial applications. More specifically, the invention relates to a method for monitoring a fluid property that is consistent with contaminant content and with a lubricant's ability to control increased contaminant content while the lubricant is in use in internal combustion engines, in particular diesel engines.

The invention comprises applying a high frequency signal between electrodes immersed in the monitored fluid and measuring a fluid-dependent response to the signal. The method of the invention comprises comparing the ratio of the current-to-initial fluid response to at least one response threshold limit and comparing the ratio of the current-toaverage rate of change of fluid response as a function of fluid use to a rate threshold to determine when a fluid reaches the end of its useful life.

One feature of the invention is that the applied signal is one of the following: essentially sinusoidal of an essentially define frequency, or essentially non-sinusoidal, for example a pulsed signal, of frequency defined by the "Fourier transform" base frequency, that is the lowest frequency of a composite of sine waves that can represent the essentially non-sinusoidal signal.

One feature of the invention is that the frequency of the applied signal is predetermined as a function of apparatus electrode geometry, fluid temperature or temperature range, chemical composition of the fluid being monitored or combinations thereof.

Another feature of the invention is that for fluids that operate over a limited temperature, preferably less than 5° C., more preferably less than 2° C., and most preferably less than 1° C., the fluid response can be measured without controlling fluid temperature or without converting or correcting the response for the effect of temperature variation.

Another feature of the invention is that the fluid response can be measured by controlling the fluid temperature to an essentially fixed temperature or can be converted or corrected to minimize the effect of temperature variation on fluid response using appropriate formulae or look-up tables.

Another feature of the invention is that a formula or look-up table used to convert or correct fluid responses for temperature variations can be permanently fixed, or can be updated, by values inputted to the method or automatically determined by measuring response changes as the fluid changes temperature between two temperature thresholds at greater than a set rate, to allow for changes in formulation of fresh fluid, that is, unused fluid, added to the equipment.

Another feature of the invention is that the threshold limits for the ratio of current fluid response to initial responses can be predetermined, or can be updated by external input to allow for changes in formulation of fresh fluid added to the equipment.

Another feature of the invention is that the average response rate increase as a function of fluid use can be fixed, can be updated by external input or can be determined by averaging the fluid response change over an initial period of fluid use.

Another feature of the invention is that essentially complete fluid exchanges made to the equipment can be determined without need for additional input in order to reset the fluid condition and quality thresholds for the fresh fluid added to the equipment.

Another feature of the invention is that an output can be provided when the fluid has reached the end of its useful live, when the fluid is near the end of its useful life, the approximate amount of contaminant in the fluid, an approximation of the remaining useful life of the fluid, response and use data for off-line analysis, or combination thereof.

Another feature of the invention is that the invention can provide an output to memory for later download, to a signaling device than can be observed or received by, for example an operator, to a service facility or function, to a signal processor that converts the output to another output, or combinations thereof.

The present invention may be more readily apparent from the following figures.

BRIEF DESCRIPTION OF THE FIGURES

FIG. 1 is a schematic representation of an apparatus that can be used with the present invention, where the apparatus controls fluid temperature.

FIG. 2 is a schematic representation of an apparatus, wherein the fluid temperature is monitored but not controlled.

FIG. 3 is a schematic graphic representation of a sinusoidal signal that can be applied to a fluid by an apparatus of the present invention.

FIG. 4 is a schematic graphic representation of a non-sinusoidal signal that can be applied to a fluid by an apparatus of the present invention.

DETAILED DESCRIPTION OF THE INVENTION

Figure 5:
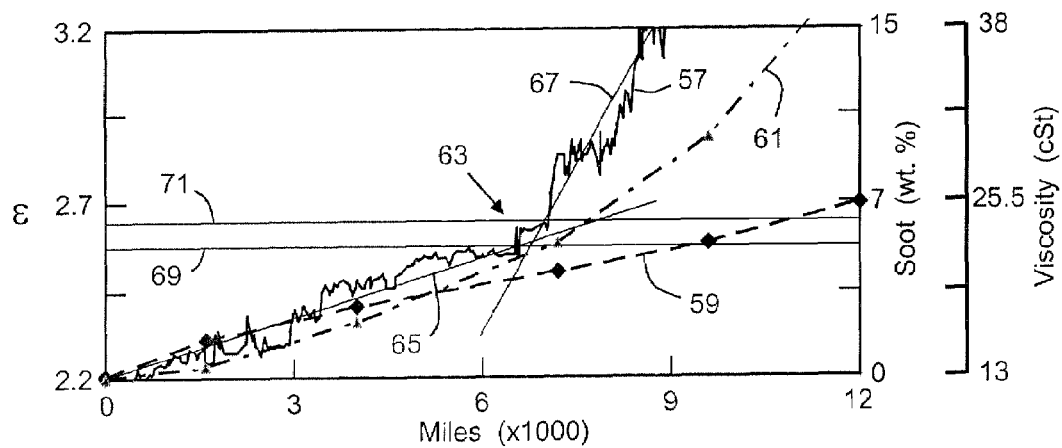
FIG. 5 is a schematic graphic representation of the high-frequency permittivity ($\epsilon$) response, soot content and viscosity of a standard-grade heavy-duty diesel engine oil as a function of engine use time.

The invention relates to a method for on-line monitoring and/or detecting condition of a highly resistive fluid used in industrial and transportation. The highly resistive fluid is a non-aqueous fluid, that is, not water based, and substantially water free. The non-aqueous fluid may, however, contain water contaminants.

FIG. 1 is a schematic illustration of an apparatus 1 that can be used to collect appropriate data required for the on-line monitoring and detecting condition of a fluid. Apparatus 1 includes essentially parallel electrodes 3 immersed in highly resistive fluid 5, in conduit 7. Electrodes 3 are fixedly held and electrically isolated by mounts 9. Apparatus 1 also includes signal generator 11 that supplies a high-frequency voltage signals of fixed amplitude and frequency through electrical conduits 13, to electrodes 3. The voltage signal supplied by signal generator 11 can be an essentially sine wave signal as shown in FIG. 3 where the voltage signal oscillates essentially sinusoidally about zero volts with the number of complete oscillations per time being the frequency of the signal. The voltage signal supplied by signal generator 11 can be non-sinusoidal as shown in FIG. 4 where the voltage signal oscillates about zero volts with a frequency defined by the Fourier transform base frequency as known in the art. The frequency of signal generator 11 is preset based on the geometry of electrode pair 3 and by type and operating temperature or temperature range and chemical composition of fluid 5. The required frequency increases as a function of the electrode area divided by the separation of electrodes 3. The frequency also increases as a function of the temperature of the fluid. The frequency variation as a function of fluid composition is quite complex and is often determined on a fluid-by-fluid basis. In one embodiment for a typical organic based fluid, at an operating temperature in the range from about 40° C. to about 120° C., using parallel-plate electrodes with an area to gap ratio of about 300 cm, the preset high frequency of signal generator 11 is on the order of 1 MHz. In another embodiment, for typical electrodes, temperature ranges and fluids 5, the preset high frequency of signal generator 11 is typically in the range from about 10 kHz to about 10 MHz. Again referring to FIG. 1, one electrical conduit 13 of signal generator 11 is grounded for a voltage reference and the other conduit 13 includes a current sensor 15, which measures electrical current flow through conduit 13. Apparatus 1 also includes controller 17 with electrical conduit 19 for powering signal generator 13, electrical conduit 21 for monitoring output voltage of signal generator 13, and electrical conduit 23 for monitoring current flow measured by current sensor 15. Controller 17 also has electrical conduit 25 to receive power and electrical conduit 27 to communicate information either to or from the controller 17.

Apparatus 1 includes a temperature controller 29, thermocouple 31, and heater 33. Thermocouple 31 and heater 33 are fixedly held in conduit 7 by mounts 35 and 37, respectively and electrically communicate with temperature controller 29 via electrical conduits 39 and 41, respectively, such that in operation controller 29 applies power to heater 33 through conduits 41 to maintain the temperature of the fluid 5 flowing past the thermocouple 31 at a determined fixed temperature; thereby maintaining the fluid temperature at electrodes 3.

In operation, fluid 5 flows through conduit 7, in the direction shown by the arrow, with a portion of the fluid flowing between electrodes 3, power is applied to controller 17 through electrical conduit 25, and temperature controller 29, monitors the temperature of fluid 5 with thermocouple 31 and electrical conduit 39 and applies appropriate power through conduits 41 to heater 33 to maintain the fluid in the conduit at a preset temperature. When used with a method of this invention, the method determines when controller 17 powers signal generator 11 to apply signal through conduits 13 and electrodes 3 to fluid 5. The electrical response of fluid 5 to the applied signals causes current to flow and to be measured by current sensor 15. Controller 17 monitors the applied signal and the corresponding current flow through electrical conduits 19, 21 respectively, and compares magnitude and phase of the voltage and current signals to calculate electrochemical impedance of the fluid 5. The method of this invention uses the impedance data to determine condition of fluid 5. Controller 17 can receive information used in the method of this invention through electrical conduit 27, for example, information that an essentially complete fluid exchange has occurred or information that is used in the determination of fluid condition can be received. A method of this invention can communicate information about the fluid condition determination from controller 17 through electrical conduit 27. The fluid condition information can be immediately communicated to a signaling device, for example a warning light, to alert an equipment operator, to a central maintenance facility to notify maintenance personnel when fluid maintenance is needed, or to a signal processor that can convert the information to other output, for example a signal that can turn equipment using the fluid "off" to prevent damage. The fluid condition information can be communicated from stored memory when queried by, for example, a service technician's diagnostics system.

While FIG. 1 shows electrodes 3 of apparatus 1 in conduit 7 with flowing fluid 5, apparatus 1 can be mounted in any location where fluid 5 flows between electrode pairs 3 in a manner that allows the fluid 5 between the electrodes 3 to be, at all times, maintained at a fixed temperature and representative of the current condition of the fluid 5 in the equipment being monitored. For example, apparatus 1 can be mounted in a fluid reservoir or sump where the heater 33 is located in close proximity to the electrodes 3 and the motion of fluid 5 is sufficient to allow appropriate heating and relatively uniform mixing and exchange of fluid within the equipment.

While FIG. 1 shows electrodes 3 to be flat rectangles with essentially only one surface of each electrode applying a signal from a signal generator to the fluid between the electrodes, in another embodiment the electrodes can have other geometry including but not limited to, for example concentric-cylinders, flat with a multitude of finger-like sections, and an apparatus embodiment can have electrodes with multiple surfaces, surface sections, which may or may not directly face surface sections of the other electrode for applying a signal to the fluid, inter-digitated electrodes where finger-like sections of one electrode alternate with finger-like sections of the other electrode and the like.

FIG. 1 shows apparatus 1 with no communication between temperature controller 29 and controller 17. In another embodiment the apparatus can have communication between the two controllers such that the method of this invention can use temperature information when determining fluid condition or so that information about required fluid temperature can be communicated to the temperature controller 29.

FIG. 1 shows apparatus 1 as individual components. In another embodiment apparatus 1 can integrate components into a compact package, which, for example reduces cost, size and/or power requirement of the apparatus. In another embodiment apparatus 1 can be incorporated into a package with other components, for example other fluid sensors, that either can work in conjunction with or independent of the components of this invention.

FIG. 2 is a schematic illustration of another embodiment of the invention, apparatus 43 that can be used to collect appropriate data. Apparatus 43 includes electrodes 3 immersed in highly resistive fluid 5 flowing in conduit 7. Electrodes 3 are fixedly held in and electrically isolated from conduit 7 by mount 9. Apparatus 43 also includes signal generator 11 applying a high-frequency voltage signal of fixed amplitude and frequency through electrical conduits 13 to electrodes 3. One electrical conduit 13 of signal generator 11 is grounded for a voltage reference and the other conduit includes a current sensor 15 that measures electrical current flow through the conduit. Apparatus 43 includes thermocouple 31 immersed in fluid 5 and fixedly held in conduit 7 by mount 35. Apparatus 43 further includes controller 17 with electrical conduit 19 for powering signal generator 13, electrical conduit 21 for monitoring output voltage of signal generator 13, electrical conduit 23 for monitoring current flow measured by current sensor 15, and electrical conduit 45 for monitoring the temperature of fluid 5 measured by thermocouple 31. Controller 17 also has electrical conduit 25 to receive power and electrical conduit 27 to communicate information. Unlike apparatus 1 of FIG. 1, apparatus 43 does not include means for maintaining the temperature of fluid 5.

In operation, fluid 5 flows through conduit 7 and between electrodes 3, power is applied to controller 17 through electrical conduit 25. When used with a method of this invention, the method determines when controller 17 powers signal generator 11 to apply signal through conduits 13 and electrodes 3 to fluid 5. The electrical response of fluid 5 to the applied signal causes current to flow and to be measured by current sensor 15. Controller 17 monitors the applied signal and the corresponding current flow through electrical conduits 19, 21 respectively and compares magnitude and phase of the voltage and current signals to calculate electrochemical impedance of fluid 5. Controller 17 also monitors thermocouple 31 through electrical conduit 45 to determine temperature of fluid 5. In one embodiment method of this invention uses the impedance data to determine condition of fluid 5 and can communicate information about that determination from controller 17 through electrical conduit 27. Controller 17 can receive information used in the method of this invention through electrical conduit 27, for example, information that an essentially complete fluid exchange has occurred or information that updates formulae or look-up tables for converting variable temperature data to constant temperature data can be received. A method of this invention can communicate information about the fluid condition determination from controller 17 through electrical conduit 27 as described for apparatus 1 of FIG. 1.

In another embodiment apparatus 43 of FIG. 2 can be mounted in locations other than conduit 7 as long as fluid 5 flows between electrode 3 in a manner that allows the fluid 5 between the electrode pairs to be at the temperature measured by thermocouple 31 and representative of the current condition of the fluid 5 in the equipment being monitored. The electrodes 3 need not be flat plates with only one surface of each electrode opposed to the other electrode. In another embodiment the apparatus can have electrode geometries with greater than one surface of each electrode opposed to the other electrode. Apparatus 43 can be individual components, as shown in FIG. 2, or can be integrated components or integrated with components other than those of apparatus 43, which, for example, reduce cost, size and/or power requirements of the apparatus.

While apparatus 1 of FIG. 1 has a means for controlling the temperature of fluid 5 and apparatus 43 of FIG. 2 has a means for determining the temperature of fluid 5, in applications where the average fluid temperature is relatively constant, preferably varying less than 5° C., more preferably varying less than 2° C., and most preferably varying less than 1° C., an apparatus similar to apparatus 43 of FIG. 2 but without thermocouple 31 and where controller 17 does not monitor the temperature of fluid 5 as electrodes 3 apply a signal to the fluid can be used with another embodiment of the method of the present invention.

FIG. 5 shows high frequency permittivity ($\epsilon$) 57, soot content 59 and viscosity 61 of a typical standard-grade heavy-duty diesel engine lubricant as a function of vehicle mileage for an heavy-duty diesel engine in a commercial vehicle that is used to test the "soot performance" of engine oils. Mileage is the distance driven since the last oil change and is a measure of engine oil use. Permittivity 57 was determined from the temperature corrected engine oil response to about a 500 kHz essentially sinusoidal voltage signal applied to electrodes immersed in the fluid. The electrodes had an area to gap ratio of about 50 cm. Fluid response was measured about every 20 seconds of engine operation. Curve 59 connects laboratory determined soot content of oil samples removed from the engine at the mileages shown, and curve 61 connects laboratory determined viscosity of the same samples.

The soot increase shown by curve 59 of FIG. 5 is relatively linear as a function of miles driven. In general, in most applications the rate of soot increase need not be linear since soot generation is not only a function of the engine type and condition, but is also dependent on fuel, operating environment and operating cycle of the engine. For the test vehicle, fuel and operating conditions are controlled to achieve an approximately 7% soot loading of the lubricant at about 12,000 miles. The viscosity increase of curve 61 is quite small during about the first 1,500 miles, relatively linear increase to approximately 6,000 miles, and then a more rapid increase starting between approximately 7,000 and about 10,000 miles. In general, although not shown in FIG. 5 since oil samples were not taken sufficiently frequent, a heavy-duty diesel lubricant shows a slight initial viscosity drop during the first several hundred miles of use caused by shearing in the engine. After the initial decrease, a heavy-duty lubricant viscosity increases primarily due to soot content increase. In particular, increasing soot content causes the viscosity to increase in a relatively linear manner as the oil additives keep the soot in small, well dispersed particles until the soot content reaches a level where the oil cannot suspend or handle all of the soot in finely divided particles. As the soot content increases beyond the point where significant quantities of larger, agglomerated soot particles begin to form, viscosity as a function of soot content ultimately begins a more rapid increase. The lubricant of FIG. 5 has a viscosity "break" occur between the oil sample taken at 7,000 miles and the sample taken at about 10,000, which contained approximately about 4.5% and about 5.5% soot respectively. The point at which a lubricant loses the ability to handle the soot and where the viscosity breaks is a function of both the lubricant formulation and operating conditions, and is not directly related to a specific soot content as will be shown in the following Figures. When the lubricant can no longer handle the soot, and in particular when the viscosity begins a more rapid increase as a function of use, the lubricant has reached the end of its useful life and needs to be replaced with fresh lubricant to allow for maximum engine performance and life.

Referring now to curve 57 of FIG. 5, the lubricant's high frequency permittivity increases at a relatively low rate, approximated by line 65, until a point marked with arrow 63 at approximately 6,500 miles, after which the permittivity increases at a more rapid rate, approximated by line 67. Before point 63 there is a relatively constant ratio between permittivity 57 and soot 59 such that the permittivity response can be used to provide an approximate value of soot content. Point 63 is consistent with where the lubricant condition is such that additional soot is not maintained in dispersed small particles, and is shown to precede the viscosity break point of the lubricant.

In U.S. application Ser. No. 10/271,885, entitled "Method for on-line monitoring of quality and condition of non-aqueous fluids", Lvovich et al disclose a method to determine fluid condition based on thresholds for fluid impedance measurements at a multitude of frequencies, including high frequency permittivity increase thresholds, incorporated by reference herein. As an example of this method, for the fluid of FIG. 5, threshold 69 could be set such that when the high frequency dielectric exceeds threshold 69 the method indicates that the lubricant needs to be "changed soon" since when permittivity 57 crosses this threshold at approximately 6,500 there is sufficient warning of a needed lubricant change before the viscosity break in the oil. Similarly, threshold 71 could be set such that when the high frequency permittivity 57 exceeds the threshold at approximately 7,000 miles the method indicates that the lubricant needs to be "changed now" since this occurrence is consistent with when the viscosity break occurs. In the previous Lvovich et al method, thresholds set at another frequency to protect against the fluid losing the ability to continue to disperse additional quantities of soot before reaching thresholds 69 and or 71. Hence, when appropriately set for a particular application, the high frequency thresholds 69, 71 used in conjunction with impedance measurements made at other frequencies signal offset voltages are sufficient for a fluid condition determination. When a high frequency impedance sensor is used alone to monitor the soot condition of a lubricant, the use of thresholds 69, 71 do not assure optimizing the oil change interval to minimize oil change cost while maximizing engine protection.

Figure 6:
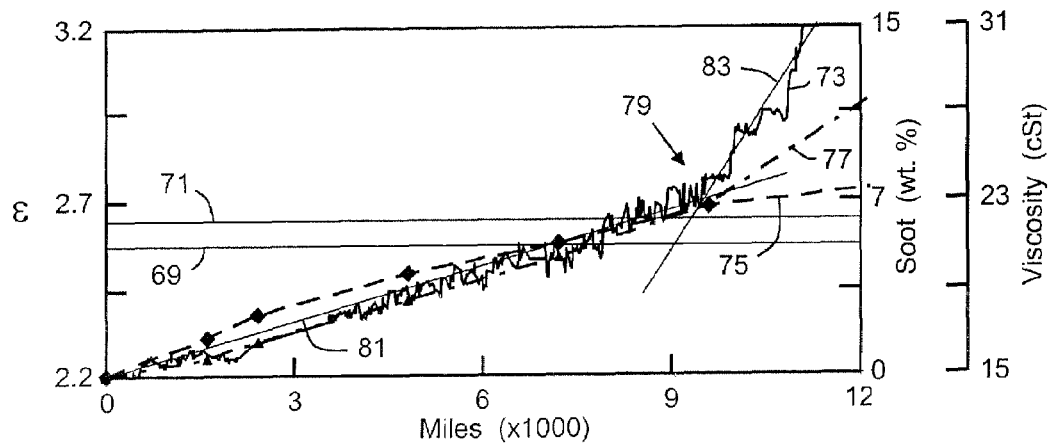
FIG. 6 is a schematic graphic representation of the high-frequency permittivity ($\epsilon$) response, soot content and viscosity of a premium-grade heavy-duty diesel engine oil as a function of engine use time.

FIG. 6 shows temperature-corrected, high-frequency permittivity 73, soot content 75 and viscosity 77 of a premium grade diesel engine lubricant as a function of vehicle mileage in the same engine, vehicle and test cycle used for the lubricant of FIG. 5. Curve 75 shows approximately the same soot content increase as curve 59 of FIG. 5. The viscosity curve 77, however, shows that this premium lubricant's viscosity does not break until in excess of approximately 10,000 test miles where the lubricant's soot concentration is approximately 7%. That is, this premium grade lubricant can disperse or handle higher concentration of soot than the standard grade lubricant of FIG. 5. Preceding the viscosity break, the high frequency permittivity curve 73 shows a rate change at point 79 where the rate of permittivity change as a before that point, approximated by line 81, is less than the rate after that point, approximated by line 83. Point 79 is consistent with where the lubricant can no longer maintain additional soot in dispersed small particles. The relatively constant ratio between permittivity 73 and soot content 75 before point 79 is consistent with the ratio of FIG. 5.

Thresholds 69 and 71 of FIG. 6 are the same as used for the standard grade lubricant of FIG. 5, and whereas the lubricant of FIG. 5 exceeds the first threshold at approximately 6,500 miles and exceeds the second threshold at approximately 7,000 miles the premium lubricant exceeds the thresholds at approximately 7,500 miles and approximately 8,500 miles respectively. Thus, using the threshold method alone the premium grade lubricant can provide an additional approximately 1,500 miles of service relative to the standard grade lubricant. To completely optimize the change interval based on the high frequency impedance measurement alone, however, depending of engine or equipment manufacturer's recommendations the lubricant may be considered useful until point 79 preceding the viscosity break, which would allow an additional approximately 500 miles of service from the premium oil before replacing the lubricant with fresh fluid.

While information about permittivity rate change point 79 of FIG. 6 may offer an option, depending on an engine manufacturer or operator specification, of further extending drain for a premium oil, a case where high-frequency permittivity rate change information is of particular value in protecting engine performance/life when only a single sensor is used is where a particular lubricant is not of adequate quality for a particular application. That is, where a lubricant should be replaced before the lubricant's high frequency permittivity exceeds thresholds optimized for a standard lubricant.

Figure 7:
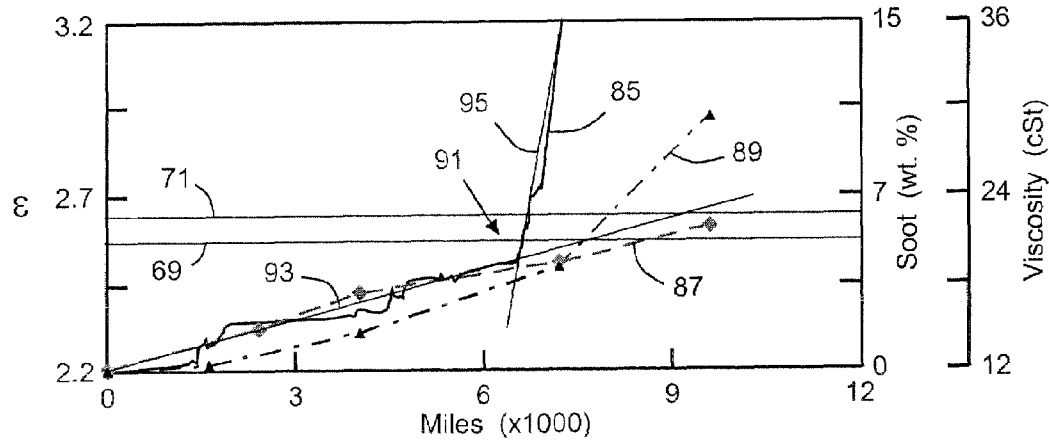
FIG. 7 is a schematic graphic representation of the high-frequency permittivity ($\epsilon$) response, soot content and viscosity of a heavy-duty diesel engine oil that was found to give poor performance in use as a function of engine use time.

FIG. 7 shows temperature-corrected, high-frequency permittivity 85, soot content 87 and viscosity 89 of a diesel engine lubricant that was found to have poor performance in particular applications. The lubricant was tested in the same engine, vehicle and operating cycle as the standard and premium lubricants of FIGS. 5 and 6, respectively. Soot curve 87 shows approximately the same soot content increase as for the previous oils. Viscosity curve 85 shows a viscosity break between the sample taken at approximately 7,000 and the sample taken at approximately 10,000 miles which contain approximately 4.5% and 5.5% soot respectively, similar to the standard grade lubricant of FIG. 5. Preceding the viscosity break, the high frequency permittivity curve 85 shows a point 91 where the rate of permittivity change as a function of mileage before that point 91, approximated by line 93, is less than the rate after point 91, approximated by line 95. Point 91 is consistent with where the lubricant can no longer maintain additional soot in dispersed small particles. The relatively constant ratio between permittivity 85 and soot 87 is consistent with the rations of FIGS. 5 and 6.

Thresholds 69 and 71 of FIG. 7 are the same as shown for the standard and premium grade lubricants of FIGS. 5 and 6, and while permittivity curve 85 crosses both thresholds before the viscosity break occurs, an earlier indicator of the lubricant's end of life was point 91 where the slope of permittivity curve 85 changed. Hence, to protect against lubricant's that may have poor performance in a particular application when using only a high frequency dielectric sensor, either thresholds 69 and/or 71 need to be set lower, which does not allow for optimizing lubricant change with standard or premium grade lubricants, or, by using the method of this invention, information about a change in slope of the fluid's high frequency permittivity at point 91 can be used to optimize the change interval.

As seen in FIGS. 5, 6, 7, the ratio between the change in high frequency permittivity curves 57, 73, and change in soot content in soot curves 59, 75 and 87 respectively is approximately the same until the permittivity rate changes of points 63, 79, 91 respectively. This is found to be true for all fluid formulations tested in this manner. Hence, until the high frequency rate change the permittivity response can be used to approximate the soot content of the oil assuming that soot is the major contaminant of the oil. Not all engines and/or applications, however, have the same ratio between permittivity change and soot change. Other contaminants can affect the fluid's permittivity response, and there are often differences in the chemical and physical properties of soot produced by different types of engine.

Figure 8:
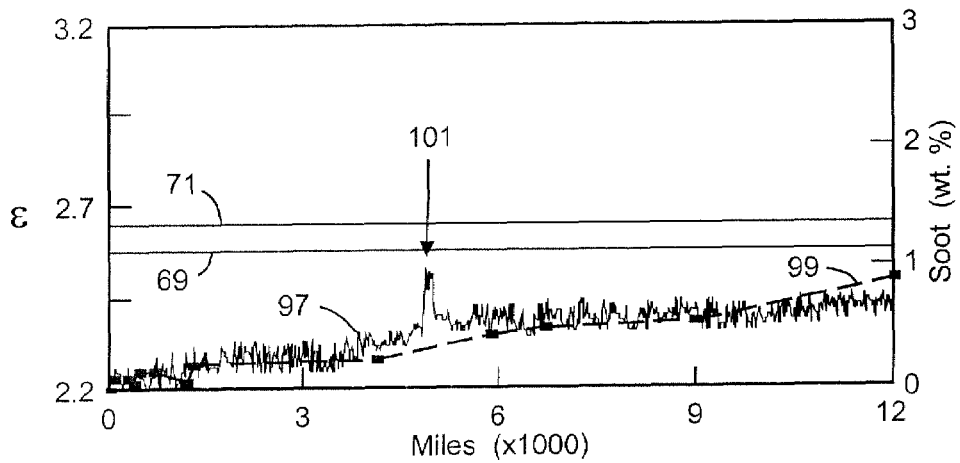
FIG. 8 is a schematic graphic representation of the high-frequency permittivity ($\epsilon$) response and soot content of a premium passenger-car engine oil that had water condensation contaminate the oil during use.

FIG. 8 shows the high frequency permittivity ($\epsilon$) 97 and soot content 99 of a typical premium-grade passenger-car diesel engine lubricant as a function of vehicle mileage for a diesel engine that is known to produce little soot during normal operation in a passenger car. As for the test results shown in FIGS. 5, 6,7, mileage is the distance driven since the last oil change and is a measure of engine oil use. Permittivity 97 was determined from the temperature corrected engine oil response to the same signal applied to the same electrode geometry at about the same 20 seconds of engine operation as before. Curve 99 connects laboratory determined soot content of oil samples removed at the mileages shown. The major difference between the passenger car test data of FIG. 8 and the commercial vehicle tests of FIGS. 5, 6, 7 is that the passenger car was not operated to test the "soot performance" of engine oils. Hence, the passenger car's operating cycle was varied and the oil testing did not continue to or beyond the viscosity break of the oil. Although not shown, the laboratory determined viscosity did not show a viscosity break during testing, and the oil ultimately reached the end of its useful life due to factors other than those related to soot or viscosity.

Referring to FIG. 8, the ratio between the increase of high frequency dielectric shown by curve 97 and the increase of soot shown by curve 99 is relatively constant. While different that the ratio shown in FIGS. 5, 6, 7, for the engine in this application, the permittivity response can be used to approximate the soot content. FIG. 8 also shows a spike in high frequency permittivity that occurred at point 101 of curve 97. The sharp rise of the peak was noted at vehicle start-up after sitting unused in a cool garage for a three day period where outside temperature and humidity had a very rapid rise. Condensation was noted on surfaces in the garage and the oil was found to have approximately 0.1% water contaminant which did not cause the oil to exceed a contaminant condemnation limit. After the increase at point 100, the permittivity returned to a normal value after the water volatilized as the oil heated during operation.

The high frequency permittivity also detects water and/or coolant contaminants. Thus, in applications where some water condensation may occur, an embodiment of the present invention can allow for transient/reversible permittivity rate changes that do not exceed a contaminant condemnation limits, to prevent a false determination of the end of a fluid's useful life. Another embodiment of the invention can recognize such transient/reversible permittivity rate change at start-up and can provide an output that the lubricant contains a contaminant until the high frequency dielectric returns to approximately the value before the contaminant was detected. Another embodiment of the invention can recognize such transient/reversible permittivity changes after each cold-start, that is when the engine is started after having been "off" for a sufficiently long period that the engine and lubricant are at approximately ambient temperature, and can provide an output that a coolant leak is possible. In each embodiment, continued permittivity rate change due to a high permittivity that exceeds permittivity thresholds is recognized by the method and warning is given of the fluid condition due to contamination content.

FIGS. 5, 6, 7, 8 plot high frequency permittivity as a function of mileage and the slopes of permittivity curves 57, 73, 85, 97 for the respective figures are described as permittivity change per change in mileage. In general, the rate of permittivity change whether measured in change per miles, per time of operation, per energy consumed (e.g. fuel use) or per energy output (e.g. work) shows a significant change in permittivity slope as at points 63, 79, 91 of FIGS. 5, 6, 7 respectively when the lubricant is no longer capable of handling a contaminant increase. Identifying the change is independent of the use cycle, as long as the "current" dielectric change as a function of use is appropriately averaged. For applications where the use cycle is relatively long and the use condition is relatively constant, as in the cases of FIGS. 5, 6, 7 the "current " slope may be averaged if in miles over several miles, if in time over several minutes and if in fuel over portions of a gallon. For applications where the use cycle is relatively short and use condition can very widely, the "current" slope may need to be averaged over longer use periods. Such averaging is known in the art. Hence, while permittivity slope is shown in FIGS. 5, 6, 7, 8 as a change in permittivity per change in mileage and for simplicity is described in the embodiments of the invention as a change in permittivity per change in time, as used herein, a permittivity slope is the change in a lubricant's high frequency permittivity response as a function of any use parameter averaged over a appropriate use interval. High frequency permittivity thresholds such as thresholds 69, 71 of FIGS. 5, 6, 7 depend on use variables only in that the fluid permittivity response is, as known in the art, averaged or filtered over sufficient use to minimize noise and other variability that affects the measured response for a meaningful comparison between the determined permittivity value and the threshold value.

Although not shown in FIGS. 5, 6, 7, 8, additions to a engine's lubricant during use to compensate for lubricant lost or consumed during operation before the point where the lubricant's permittivity slope changes simply lower the permittivity value, extending mileage or operating time until the lubricant's high frequency permittivity exceeds the thresholds 69, 71 or reaches a point where the permittivity slope changes due to the end of the lubricant's useful life for controlling contaminants. Such additions do not significantly change the slope of the permittivity curve and any change is substantially smaller that the slope change that occurs when the lubricant loses the ability to adequately handle additional quantities of soot.

Although the initial high frequency permittivity of the lubricants of FIGS. 5, 6, 7, 8 are approximately the same, all lubricant's do not have the same initial permittivity value. Only the relative increase of permittivity value and the slope change are important in determining the condition of a fluid. In general, however, fresh lubricant's have a lower permittivity than used lubricants; hence a complete oil change can be detected by a substantial drop in permittivity value.

FIGS. 5, 6, 7, 8 show high frequency permittivity for lubricant response that is corrected for lubricant temperature variations that occur during test vehicle operation. In general, fluid impedance values are temperature dependent and either controlling fluid temperature or correcting for temperature variations allows for the most accurate interpretation of fluid condition. However, some applications may have a sufficiently narrow fluid operating temperature range or may have a predictable temperature cycle that allows use of the data without temperature control or correction based on measured fluid temperature. In general, if the response data is not corrected, the temperature range of the fluid response measurement is preferably less than 5° C., more preferably less than 2° C., and most preferably less than 1° C.

Figure 9:
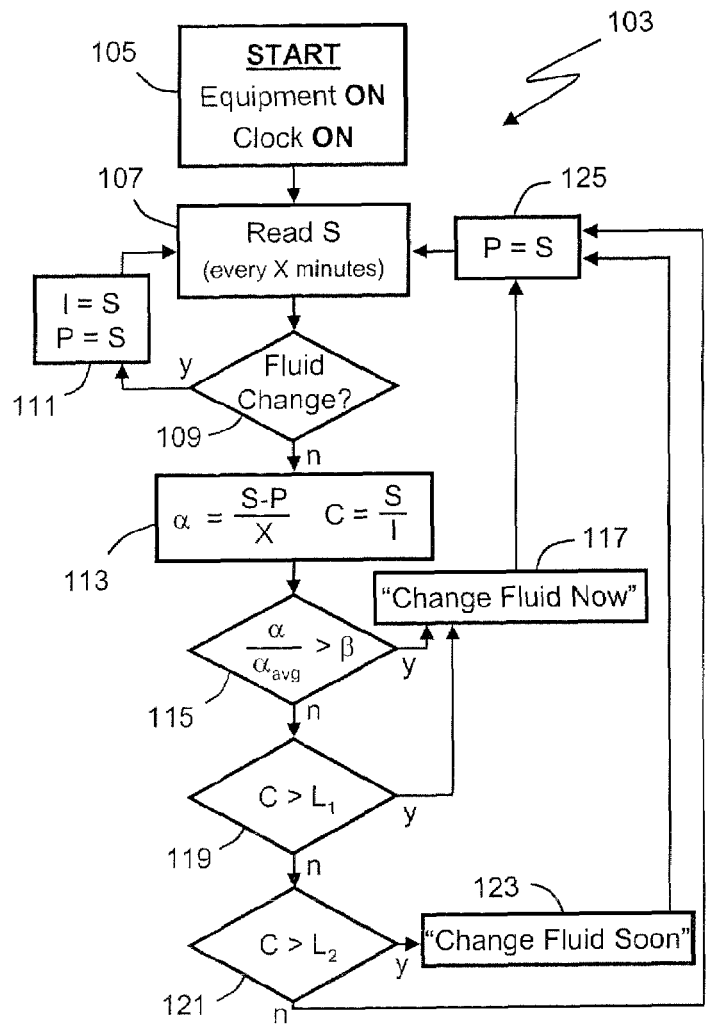
FIG. 9 is a flow chart of a feature of the present invention wherein high-frequency dielectric response data, which are not corrected for temperature, determine when a fluid is approaching the end of its useful life and when the fluid has reached the end of useful life.

FIG. 9 shows another embodiment 103 of a feature of the present invention that uses the above described high frequency permittivity to determine the condition of a fluid in equipment where the fluid is maintained at a relatively constant temperature for condition determination. The temperature can be maintained either by the fluid measurement apparatus, for example apparatus 1 in FIG. 1, or by the equipment or a means associated with the equipment in which the fluid is used.

Method 103 begins in block 105 each time the equipment is started, i.e. turned "on" where a clock that outputs time is also turned "on". In this embodiment time is the measure of equipment use that is used to determine the slope of permittivity change; however, as previously described in other embodiments can have another use variable such as mileage, fuel consumed, energy output or combination thereof that can be measured by or inputted to the method.

After start-up method 103 proceeds to block 107 to read fluid response S to an applied high-frequency signal. Signal S is obtained by a fluid measurement apparatus of the type described in association with FIG. 1. S can be a permittivity value as shown in FIGS. 5, 6, 7, or values that are essentially equivalent. For example, instead of converting the fluid responses to values with appropriate dimensional units, analogue voltages, currents or digital inputs can be read that can be converted to appropriate fluid responses. As another example, the permittivity response may be received as impedance and phase angle signals. S can be data collected by the apparatus over a short period of time with no filtering, or can be averaged over a longer period of time and filtered to minimize noise and to better quantify fluid's high frequency permittivity response. In any case, while the equipment is "on" the method reads S in block 107 at fixed intervals of "X" minutes to determine fluid quality.

After input S is read, method 103 in block 109 determines if an essentially complete fluid change occurred since the last time S was read. This determination can be based on an input to the method. For example, a maintenance person, or operator, could provide a signal when a fluid change is made that is communicated to the controller (e.g. by electrical conduit 27 to controller 17 of apparatus 1 in FIG. 1) and detected in block 109. As another example, a sensor or sensor system that detects fluid change either by fluid level changes or by other means could provide a signal that is detected in block 109. The determination of block 109 can also be made using input S and no additional input to identify the fluid change; an example of which will be shown in a later embodiment of the invention. If the determination in block 109 is "yes", then in block 111 the initial value I for the high-frequency signal determination (corresponding to the initial permittivity values of FIGS. 5, 6, 7, 8 at mileage equal to zero) is set equal to S, the variable P which is used in a permittivity slope calculation is set equal to S. After the values are set in block 111, method 103 returns to block 107 where X minutes after the previous reading, S is again read.

If the determination in block 109 is "no", method 103 advances to block 113 where the current slope a is calculated, which is the current signal S minus the previous signal P, that quantity divided by the time of operation between the signals X, and ratio C, which is current signal S to the initial signal 1, that is, the ratio used-fluid's permittivity to the permittivity when the fluid was fresh. Method 103 uses the current slope in block 115 a determination if the ratio of current slope a to an average slope $\alpha_{avg}$ is greater than a slope threshold or limit $\beta$. In this embodiment $\alpha_{avg}$ is a fixed number set based on the expected high frequency permittivity slope for a particular equipment type and/or application. $\beta$ is a fixed number set based on the maximum variation of high frequency permittivity slope increase that is expected for a fluid that is of appropriate condition to handle additional contaminant increase for a particular equipment type and/or application. If the determination of block 115 is "yes", method 103 in block 117 sends a "Change Fluid Now" warning. The warning may be sent to memory for later retrieval, to a signaling device, for example a warning light, which can alert an equipment operator, to a central maintenance facility to notify maintenance personnel, to a signal processor that converts the output to another output, or combinations thereof. If the determination of block 115 is "no", method 103 determines in block 119 whether ratio C is greater than threshold or limit $L_1$. $L_1$ is a fixed number essentially setting a limited on the maximum contamination allowed in the fluid based on an equipment manufacturer's or an equipment operator's specification for a particular equipment type and/or application. If the determination of block 119 is "yes", in block 117 method 103 sends a "Change Fluid Now" warning. If the determination is "no", in block 121 method 103 determines if ratio C is greater than a threshold $L_2$. $L_2$ is a fixed number less than $L_1$ set based on a manufacturer's or operator's specification to give ample warning that the fluid is approaching the end of its useful life as determined by block 119. If the determination of block 121 is "yes", method 103 in block 123 sends a "Change Fluid Soon" warning. If the determination in block 121 is "no", or after a warning signal is sent in either blocks 117 or 123, method 103 in block 125 sets P equal to the S and in block 107 reads a new S at a time X minutes after the previous permittivity reading and repeats the sequence of blocks 109 to 125 to determine and, as needed, report fluid condition. Method 103 continues to reading S every X minutes and making fluid condition determinations until the equipment using the fluid is turned "off". Each time the equipment is turned "on", method 103 begins in block 105.

In this manner, method 103 essentially continuously monitors the condition of a fluid and sends warnings when the fluid is either near or at the end of its useful life based on contamination content or the fluid's ability to handle the contamination content.

The embodiment of FIG. 9 reads and uses fluid response S immediately after the equipment using the fluid is turned "on". In some applications there may be transients in the signal immediately after start-up, for example due to temperature variations or moisture condensation, where some equipment operation time is needed before the fluid reaches a steady-state where high-frequency permittivity response provides more meaningful information about the fluid's contamination condition. Hence, in another invention embodiment the method need not start making fluid condition determination immediately on equipment start-up. The embodiment of FIG. 9 uses a fixed $\alpha_{avg}$ for determining whether the rate of high frequency permittivity response exceeds a limit. In another embodiment the method can calculate an average slope for the initial permittivity increase and use that slope for a determination. The embodiment of FIG. 9 simply provides a warning when the contamination content limit is approached, but gives no indication of the approximate amount of contaminant in the fluid or the approximate equipment use that remains before the contamination limit is reached. In another embodiment the method can provide information about approximate contaminant content and information about the amount of equipment use that remains before the fluid must be changed based on average operating conditions.

Figure 10:
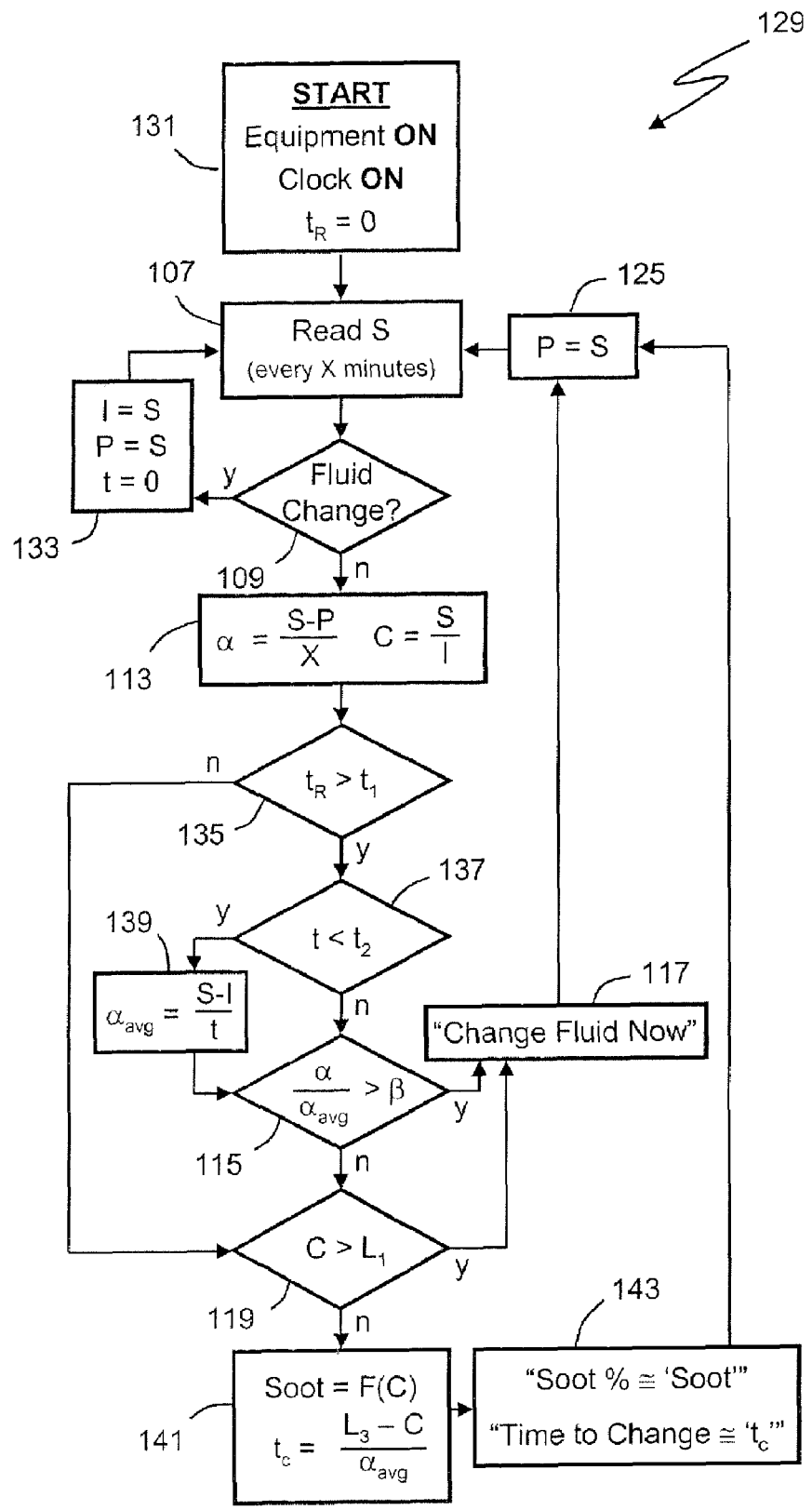
FIG. 10 is a flow chart of another feature of the present invention wherein high-frequency permittivity response data determine an approximate amount of contaminant present in a fluid, approximate use remaining before the fluid reaches the end of useful life, and warning of when the fluid has reached the end of useful life.

FIG. 10 shows an embodiment of a feature of the present invention for use in determining the condition of a fluid in equipment where the average slope is calculated by the method, slope change determination is not made immediately after start-up, and information is output about approximate contaminant content and approximate remaining useful life of the fluid. As with the embodiment of FIG. 9, this embodiment is for an application where the fluid is maintained at a relatively constant temperature. To aid in describing the embodiment of FIG. 10, those blocks that are the same as blocks in FIG. 9 are labeled the same.

Referring to FIG. 10, the method 129 begins in block 131 when the equipment is turned "on", a clock is tuned "on" and time $t_R$ is set equal to zero. This embodiment uses time as the measure of equipment use to determine the slope of permittivity change. The variable $t_R$ is a measure of the time of the current operating cycle from when the equipment is turned "on" until turned "off". After start-up, method 129 proceeds to block 107 and reads S, which is the fluid's permittivity response or an equivalent that can be averaged and/or filtered as appropriate to minimize noise and to better quantify the fluid's high frequency permittivity response and/or rate of change of response.

After reading S, method 129 in block 109 determines, as previously described, if an essentially complete fluid change has occurred since the last time S was read. If the determination is "yes", in block 133 the fresh fluid's initial permittivity value I and previous permittivity value P are set equal to S and t is set equal to zero. The variable t is a measure of total time of equipment operation since the last fluid change and thus is set equal to zero each time a fluid change is made. After the values are set in block 133, method 129 returns to block 107 where X minutes after the previous reading, S is again read.

If the determination is block 109 is "no", method 129 advances to block 113 where the current slope α and the ratio of current permittivity to initial permittivity are calculated, and in block 135 method 129 determines if the time since the start of the current operating cycle $t_R$ is greater $t_1$. Time $t_1$ is fixed number that is selected to allow the permittivity slope to reach steady state after start-up. For example, in many equipment under certain environmental and operating conditions, water condensation can contaminate the fluid while "off", resulting in an increased high-frequency permittivity that is reversed once the water is volatilized during equipment operation, as was shown and describe for FIG. 8. Hence, permittivity slope information may not be meaningful immediately after start-up. If the determination in block 135 is "yes", method 129 skips blocks 137, 139, 115 and in block 119 still determines if permittivity ratio C exceeds threshold $L_1$; thus protecting the equipment. If the determination in block 135 is "no", method 129 in block 137 determines if the total operating time since the last complete fluid change t is greater than $t_2$. Time $t_2$ is fixed number that is selected such that under even extreme operating conditions, the contamination content of the fluid should not exceed a fluids ability to control the typical contaminants. For example, $t_2$ may be selected as 50% of the typically expected useful life of the fluid. If the determination in block 137 is that "yes", in block 139 the average slope $\alpha_{avg}$ is set equal to the total high frequency permittivity change since the last complete fluid change, that is the current permittivity minus the initial permittivity, divided by the total operating time since last change. If the determination of block 137 is "no", method 129 uses the last average slope $\alpha_{avg}$ calculated in block 139 until the next complete fluid change. Method 129 in block 115 determines if the permittivity slope a calculated in block 113 divided by the average slope $\alpha_{avg}$ is greater than a slope limit β. If the determination of block 115 is "yes", in block 117, method 129 sends a "Change Fluid Now" warning. If the determination of block 115 is "no" or if the determination of block 135 is "no", method 129 determines if the permittivity ratio C calculated in block 113 is greater than threshold $L_1$. If "yes", method 129 in block 117 sends a "Change Fluid Now" warning. If "no", method 129 in block 141 determines an approximate percentage of contaminant in the fluid and determines and an approximate length of time until the fluid needs to be changed. In the embodiment of FIG. 10, the contaminant is assumed to be soot and the approximate amount of soot is determined by F(C), which is a function of the current to initial permittivity ratio. The time to required fluid change is approximated by a threshold $L_3$ minus the permittivity ratio C, that quantity divided by the average slope of the permittivity change. $L_3$ is a fixed number that is used to approximate the end of life of the fluid. $L_3$ can be set to be equal $L_1$, or may be set less than $L_1$ to provide a more conservative estimation of the fluid's remaining useful life. Method 129 in block 143 sends an output of the approximate soot content and of the approximate equipment operating time remaining until a complete fluid change is required. The output of block 143 may be sent to memory for later retrieval, to a signaling device, for example a information display, which can alert an equipment operator, to a signal processor where the information is converted to another output, for example "time to change" is converted to "miles to change", to a central maintenance facility to notify maintenance personnel, or combinations thereof. After method 129 outputs information in block 143 or sends the warning of block 117, P is set equal to S in block 125 and the method returns to read a new S in block 107 X minutes after the previous reading. Method 103 continues to read S every X minutes and mak fluid condition determinations until the equipment using the fluid is turned "off". Each time the equipment is turned "on" the method 129 begins in block 131.

In this manner, method 129 essentially continuously monitors the condition of a fluid and sends information about approximate contaminant content and approximate time to the next required fluid change, or a warning that the fluid must be changed either due to reaching a permittivity ratio threshold or a permittivity rate threshold.

The embodiments of FIGS. 9 and 10 assume that the fluid temperature does not vary as the signal S is read in block 107. The present invention, however, does not require that the fluid temperature remain constant when the fluid response is measured.

Figure 11:
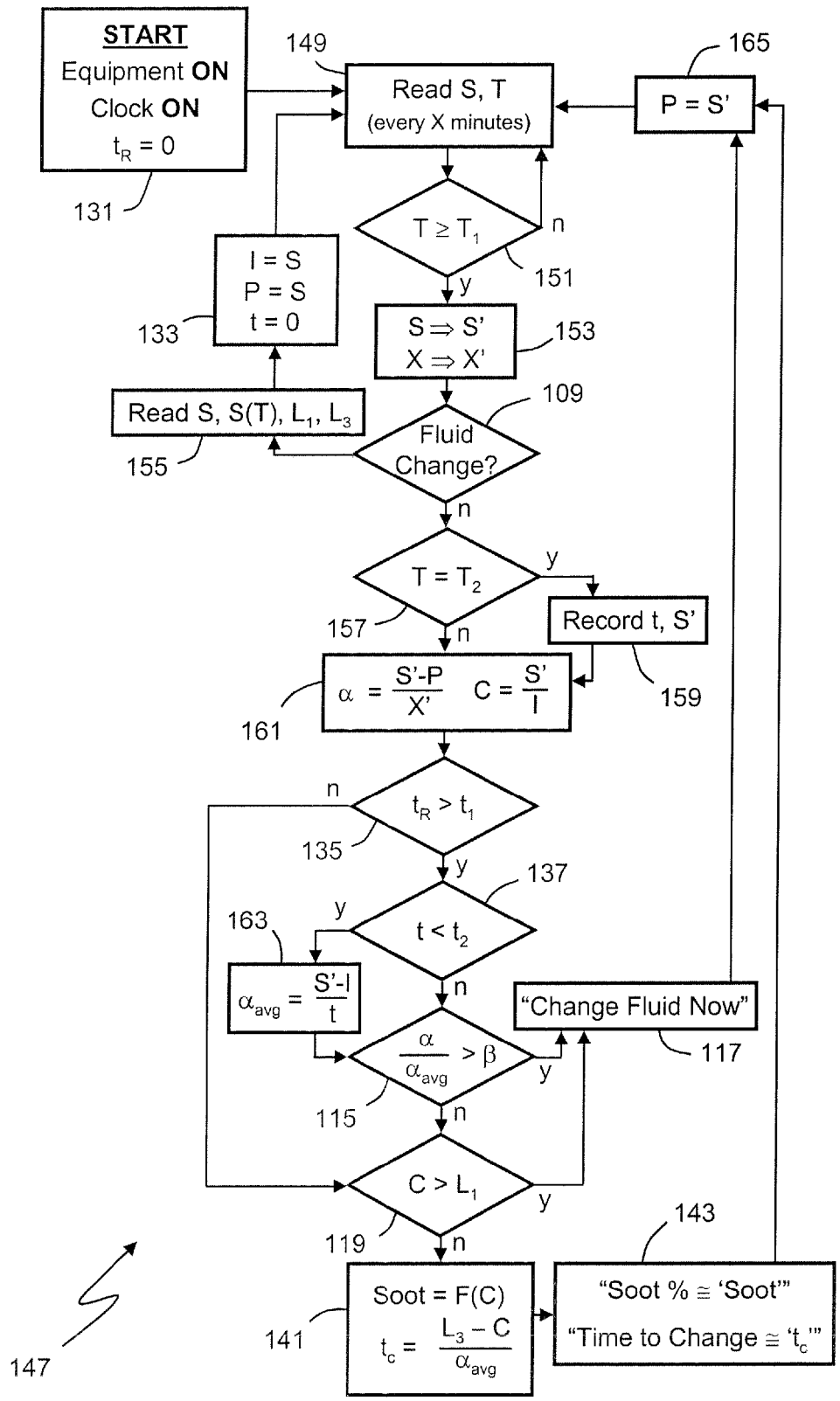
FIG. 11 is a flow chart of a feature of the present invention wherein high-frequency permittivity response data corrected for fluid temperature variations are used to determine a fluid condition.

FIG. 11 shows an embodiment of a feature of the present invention for use in determining the condition of a fluid in equipment where the fluid response S is corrected for variations of fluid temperature. To aid in describing the embodiment, those blocks that are the same as in a previous embodiment are labeled the same.

Referring to FIG. 11, method 147 begins in block 131 when the equipment is turned "on", a clock is turned "on" and time $T_R$ is set equal to zero. As in the previous embodiments, time is the measure of equipment use to determine permittivity change slope. After start-up, method 147 reads S and T in block 149. S is the fluid's permittivity response or an equivalent and T is the temperature of the fluid near or at the electrodes measured by the apparatus used to determine S. In block 151, method 147 determines if T is greater than or equal to a lower temperature limit $T_1$, which is the lowest fluid temperature where the signal S can be corrected within acceptable error limits by the temperature compensation of this method. For example, method 129 may use a linear equation for temperature compensation that only approximates the actual temperature variation of S within acceptable limits over a specified temperature range starting at temperature $T_1$ up to the maximum operating temperature of the fluid. If the determination of block 151 is "no", method 147 returns to block 149 where X minutes after the previous reading, S and T are again read. Method 147 does not progress to block 153 until the determination in block 151, that is, the fluid temperature is sufficiently high for signal S to be corrected to a fixed temperature value, is "yes". In block 153 method 147 temperature corrects signal S to signal S' using a function, a look up table or combinations there of, to allow comparison of signals taken at different fluid temperatures. Also in block 153, time interval X is temperature corrected to time X' for the signal rate determination since the rate of change of a fluid's high-frequency permittivity may vary as a function of fluid temperature. Hence, correcting X allows for a more accurate comparison of rates at different temperatures. Method 147 in block 109 determines if a fluid change has occurred. In this embodiment, the change determination is made based on a maintenance input, which in addition to providing a positive determination in block 109, provides information about the fresh lubricant that is read in block 155. That is Immediately after receiving information that a fluid change has occurred, method 147 reads information in block 155 that is inputted, for example by a keypad, optical scanner, or other means, providing the initial value of S at the desired measurement temperature, the temperature dependence S(T), which may be a function, values for a look-up table, or combinations thereof, of the signal S and the limits $L_1$ and $L_3$ that are used in determining the permittivity and therefore the contamination limits of the fluid. In block 133, method 147 sets I and P equal to S read in block 155 and sets the total run time t equal to zero for the fresh fluid. If the determination in block 109 is "no", method 147 in block 157 determines if the fluid temperature is equal to temperature $T_2$. $T_2$ is a temperature that is greater than $T_1$ where when the fluid approximately equals this temperature, a feature of this embodiment is that in block 159 method 147 records both the corrected signal S' at this temperature and the current total use time t. In general, the present invention does not need to record data other than that of the described variables; however, the invention allows for data, either temperature correct or not, to be recorded or output that can be used in a separate fluid condition analysis. After recording data in block 159 or if the determination of block 157 is "no", method 147 in block 161 calculates the current slope a using the temperature corrected S' and X', and ratio C using the temperature corrected S'. After block 161, the remainder of method 147 is the same as method 129 of FIG. 10 except that method 147 uses temperature corrected S' when calculating the average slope $\alpha_{avg}$ in block 163 and when replacing P in block 165.

In this manner, method 147 essentially continuously monitors the condition of a fluid when fluid temperature is greater than or equal to temperature $T_1$, and sends information about approximate contaminant content, approximate time to next fluid change, or a warning that the fluid must be changed either due to reaching a permittivity ratio limit associated with the fluid's contaminant content or a permittivity rate limit associated with the fluid's ability to control the contaminant.

While method 147 of FIG. 11 uses a determination if run time $t_R$ is greater than $t_1$ in block 135 to either minimize or eliminate any transient permittivity slope change that occur during start-up, in some applications, the temperature determination of block 151 may be sufficient to minimize or eliminate transient permittivity slope changes at start-up.

While method 147 of FIG. 11 allows for changing the temperature dependence S(T) of signal S in block 155, the present invention does not require that temperature dependence S(T) change when the fluid is changed. The temperature dependence S(T) can remain fixed or can be calculated by the method to account for changes in temperature dependence due either to a change to a fluid with different formulation or due to changes that occur to a fluid during use.

Figure 12:
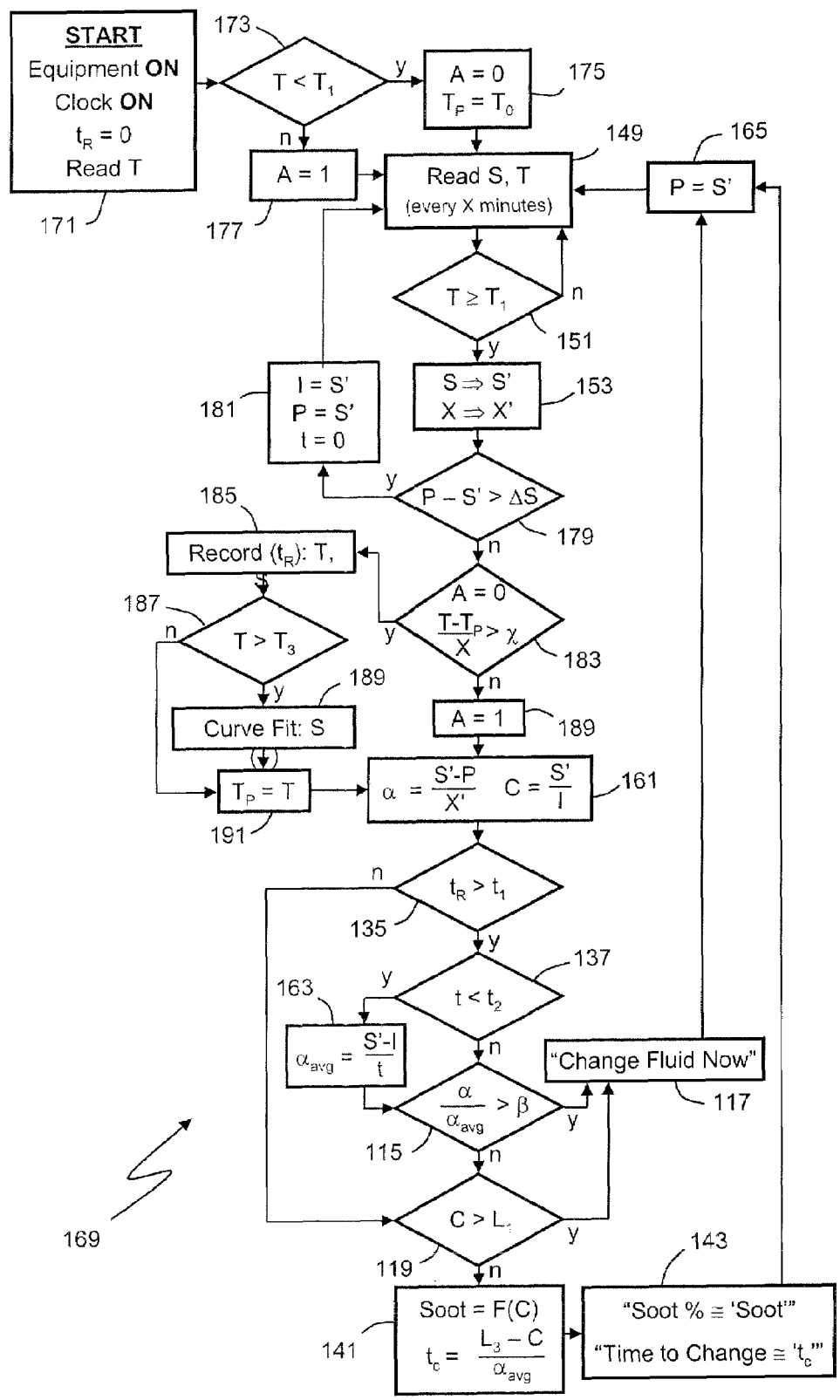
FIG. 12 is a flow chart of a feature of the present invention wherein high-frequency permittivity response data are use to determine if a fluid is replaced with fresh fluid, temperature correction for the fluid response, and the condition of the fluid.

FIG. 12 shows an embodiment of a feature of the present invention for use in determining the condition of a fluid in equipment wherein the fluid response S is corrected for fluid temperature variations using a temperature correction function S(T) that is determined by the method.

Referring to FIG. 12, method 169 begins in block 171 when the equipment is turned "on", a clock is turned "on", time $t_R$ is set equal to zero and fluid temperature T is read. Block 173 determines if the temperature read in block 171 is less than the lower temperature-correction limit $T_1$, described in embodiment 147 of FIG. 11. If the determination of block 173 is "yes", in block 175 variable A is set equal to zero and variable $T_P$ is set equal to $T_0$ where $T_0$ is a temperature that is selected to be less than $T_1$ as will be explained below. If the determination of block 173 is "no", method 169 in block 177 sets variable A equal to one. After setting variables A and $T_P$ appropriately, method 169 reads signal S and fluid temperature T in block 149, and in block 151 determines if the temperature is greater than or equal to the lower temperature-correction limit $T_1$. The method does not advance to block 153 where the signal S and time interval X are temperature compensated as variables S' and X' until the determination of block 151 is "yes". In block 179 determines if the difference between the previously stored temperature corrected signal P and the current temperature corrected signal S' is greater than value ΔS. In general, fresh fluids with different formulations can have different high-frequency impedance. In many applications, however, the differences in initial impedance values is far less than the impedance change that occurs in the fluids after even moderate use. Hence, in these applications, appropriate selection of ΔS allows block 179 to identify when a complete fluid change is made. If the determination of block 179 is "yes", method 169 in block 181 sets initial value I and previous value P equal to temperature corrected signal S' and total time of use t to zero. If the determination if block 179 is "no", in block 183 method 169 if variable A is equal to zero and if the rate of fluid temperature increase, which in this embodiment is shown as the current temperature T minus the previously measured temperature $T_P$ that quantity divided by the time interval between the two temperature measurements, is greater than a fixed rate χ The determination of block 183 is always "no" unless at start-up the fluid temperature is less than $T_1$ with A set equal to zero in block 175. Also the $T_0$ of block 175 is selected low so that the calculated temperature rate in block 183 is greater than the fixed rate χ. The rate χ is selected such that the fluid temperature increases rapidly enough so that essentially any change occurring in signal S is due to the temperature increase and not due to use related fluid changes. That is, if the determination of block 183 is "yes", method 169 uses changes in temperature T and signal S to up-date the function used in block 153 to temperature correct signal S with the assumption that all change in S is due to the temperature change; hence, the rate χ must be appropriate for the fluid and the application.

If the determination of block 183 is "yes", in block 185 the fluid temperature T and signal S, which is uncorrected signal read in block 149, are recorded, and method 169 in block 187 determines if fluid temperature T is greater than $T_3$, which is a temperature greater than $T_1$. If the determination of block 187 is "yes", method 169 in block 189 uses the recorded temperature T and signal S data to determine a new signal temperature correction function S(T). The recorded data include information from the first time method 169 steps through blocks 185 which is at temperature T approximately equal to $T_1$ because of determinations in blocks 173 and 151, to the current temperature T, which must be greater than $T_3$ as determined in block 187. Hence, a new function S(T) is calculated only if the fluid temperature increases from approximately $T_1$ to greater than $T_3$ at a rate greater than $\chi$. If the determination of block 187 is "no" or after the calculation of block 189, method 169 set $T_P$, which is used in the temperature rate calculation of block 183, to T. If the determination in block 183 is "no", method 169 in block 189 sets variable A is set equal one so that the determination in block 183 is always "no" until the next time the equipment is started with fluid temperature less that $T_1$ allowing A to be set equal to zero in block 175.

After either block 189 or block 191 method 169 in block 161 calculates rate a of signal S' change as a function of use and the ratio C of the current S' to initial temperature corrected signal I. After block 161, the remainder of method 169 is the same as method 147 of FIG. 11.

In this manner, method 169 essentially continuously monitors the condition of a fluid when fluid temperature is greater than or equal to temperature $T_1$, using a temperature compensation function S(T) which may be updated by the method, and sends information about approximate contaminant content, approximate time to next fluid change, or a warning that the fluid must be changed either due to reaching a permittivity ratio limit associated with the fluid's contaminant content or a permittivity rate limit associated with the fluid's ability to control the contaminant.

Method 169 of FIG. 12 allows for the temperature correction function to be updated only once during each equipment operating cycle, only with the fluid temperature increasing and only starting at temperature $T_1$ which is the lower temperature limit for temperature correcting signal S. The present invention is not limited to this method of automatically updating the temperature correction function or temperature correction look-up tables used to correct fluid responses for variations in temperature. Method 169 records T and S each time method 169 steps through block 185; however, if a linear temperature correction function S(T) is calculated in block 189 and used in block 153, then a similar embodiment of the invention need only record T and S the first time through a block similar to block 185 when the temperature is approximately $T_1$ and the determination of a new S(T) would use those S and T and the current S and T where the current T is greater than $T_3$.

While the embodiments shown in FIGS. 9, 10, 11, 12 show the use of two thresholds, $L_1$ and $L_2$ in FIG. 9 and $L_1$ and $L_3$ in FIGS. 10, 11, 12, the invention does not require the use of two thresholds. Other embodiments may use only one threshold, for example, an embodiment similar to that of FIG. 9 may use only threshold L1 and only give warning when the fluid must be changed, embodiments similar to those of FIGS. 10, 11, 12 can have a block similar to block 141 where instead of $L_3$, $L_1$ is used to determine time to change. Also other embodiments may use more than two thresholds to either provide additional information of fluid condition, for example, one or more thresholds may be used to determine if a signal rise at start-up is a transient due to water condensation or a small coolant leak and to determine when the contaminant is removed after the lubricant reaches an appropriate temperature, or to allow for alternate thresholds should certain performance conditions be met, for example, a calculated $\alpha_{avg}$ be found to be above or below an expected value.

While the embodiments shown in FIGS. 10, 11, 12 show embodiments that wait for the run time $t_R$ to be greater that time $t_1$ before the ratio of the current slope to average slope ($\alpha/\alpha_{avg}$) is compared to threshold $\beta$ to ignore transients that may occur during start-up, for example, due to water condensation, the invention does not require that the method wait for run time to be greater than a time threshold. Another embodiment may, for example, use transients that occur at start-up to provide an output that a contaminant exists until the slope reverses or the high-frequency signal returns to approximately the value before the transient. Another embodiment, for example, may use repeated start-up transients to provide an output that a small coolant leak may exist.

While particular embodiments of the present invention have been shown and described, it is apparent that various combinations, changes and modification may be made therein to meet fluid analysis needs of various applications without departing from the invention in its broadest aspects. In particular, with regard to various functions performed by the above described invention, the terms (including any reference to a "means") used to describe individual components or sub-systems of the invention are intended to correspond, unless otherwise indicated, to any component or sub-system which performs the specified function of the described component or sub-system (e.g. that is functionally equivalent), even though not structurally or electronically equivalent to the described component or sub-system which performs the function in the herein illustrated embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A method for determining the condition of a non-aqueous fluid comprising:
   a) applying a high-frequency voltage signal between electrodes immersed in the fluid,
   b) measuring the fluid's response to the applied signal and determining a fluid property,
   c) comparing the magnitude of the determined property, relative to the magnitude of that property when the fluid is fresh, to at least one property threshold and comparing the rate of change of the determined property, relative to the average rate of change of the property as a function of fluid use to at least one rate threshold, resulting in the determination of the fluid's condition
   wherein the determined fluid property is the fluid's permittivity and wherein said property is used to determine the fluid's condition where the pemittivity is used to determine if contaminants in the fluid are being maintained in dispersed small particles.

2. The method of claim 1 wherein the applied signal is one of the following selected from at least one of the group consisting of essentially of sinusoidal of an essentially defined frequency, essentially non-sinusoidal of frequency defined by the Fourier-transform base frequency combinations thereof.

3. The method of claim 1 wherein the frequency of the applied signal is predetermined as a function of at least one of the following selected from the group consisting of electrode geometry, fluid temperature, fluid temperature range, composition of the fluid being monitored and combinations thereof.

4. The method of claim 1 wherein the frequency is in the range of about 10 kHz to 10MHz.

5. The method of claim 1 wherein the fluid response to the applied signal is measured at essentially fixed temperature with the temperature dependent upon the fluid employed, and where the temperature variation is preferably less than 5° C.

6. The method of claim 1 wherein the fluid response to the applied signal is measured at variable temperatures in the range of ambient temperatures to maximum operating temperatures and the fluid property determination is selected from at least one of the group consisting of converting the property to essentially a fixed-temperature property, minimizing the effect of temperature variation, using; a temperature dependent formula, using a temperature dependent look-up table and combinations thereof.

7. The method of claim 6 wherein a means for converting the property to essentially fixed-temperature fluid property is selected from at least one of the group consisting of fixed, updated by external input, automatically updated when fluid temperature increases between two temperature thresholds at greater than a preset rate and combinations thereof.

8. The method of claim 1 wherein the determined fluid property is one selected from at least one of the group consisting of permittivity, permittivity equivalent and combinations thereof.

9. The method of claim 1 wherein the thresholds for comparing the determined fluid property are selected from at least one from the group consisting of fixed, updated by external input and combinations thereof.

10. The method of claim 1 that further includes resetting values used for the comparisons under the conditions selected from the group consisting of an external input is provided that a fluid change has occurred, change in the determined fluid property is used to determine that a fluid change has occurred and combinations thereof.

11. The method of claim 1 wherein the determined fluid condition is one selected from the group consisting of the fluid is near the end of its useful life, the fluid is at the end of its useful life, the fluid needs to be changed soon, the fluid needs to be changed now, the fluid contains a contaminant, an approximate amount of contaminant in the fluid, an approximate remaining useful life of the fluid, an approximate amount of use remaining before the fluid needs to be changed, or combinations thereof.

12. The method of claim 11 wherein the contaminant in the fluid comprises soot, water, engine coolant or mixtures thereof.

13. The method of claim 1 that further includes providing an output of the determined fluid condition to one selected from the group consisting of memory for later download, a signaling device, a service facility, a signal processor, or combinations thereof.

14. The method of claim 1 that further includes providing fluid response and use data for other analysis methods.

* * * * *